United States Patent

Urick

[11] Patent Number: 5,836,893
[45] Date of Patent: Nov. 17, 1998

[54] INTRAVASCULAR GUIDEWIRE

[75] Inventor: Michael J. Urick, Rogers, Minn.

[73] Assignee: SciMed Life Systems, Inc., Maple Grove, Minn.

[21] Appl. No.: 612,751

[22] Filed: Mar. 8, 1996

[51] Int. Cl.$^6$ .................................................. A61B 5/00
[52] U.S. Cl. .......................... 600/585; 600/433; 600/434
[58] Field of Search ................................ 128/772, 657–8; 604/95.6, 280.3; 606/190

[56] References Cited

U.S. PATENT DOCUMENTS

| | | | |
|---|---|---|---|
| 4,282,876 | 8/1981 | Flynn | 128/349 R |
| 4,345,602 | 8/1982 | Yoshimura et al. | 128/349 R |
| 4,456,017 | 6/1984 | Miles | 128/772 |
| 4,534,363 | 8/1985 | Gold | 128/772 |
| 4,642,267 | 2/1987 | Creasy et al. | 428/413 |
| 4,721,117 | 1/1988 | Mar et al. | 128/772 |
| 4,729,914 | 3/1988 | Kliment et al. | 428/36 |
| 4,739,768 | 4/1988 | Engelson | 128/658 |
| 4,811,743 | 3/1989 | Stevens | 128/772 |
| 4,835,003 | 5/1989 | Becker et al. | 427/2 |
| 4,867,174 | 9/1989 | Skribiski | 128/772 |
| 4,884,579 | 12/1989 | Engelson | 128/772 |
| 4,899,787 | 2/1990 | Ouchi et al. | 128/131 |
| 4,922,924 | 5/1990 | Gambale et al. | 138/772 |
| 4,925,445 | 5/1990 | Sakamoto et al. | 604/95 |
| 4,955,862 | 9/1990 | Sepetka | 604/164 |
| 4,961,731 | 10/1990 | Bodicky et al. | 604/264 |
| 4,977,901 | 12/1990 | Ofstead | 128/772 |
| 4,991,602 | 2/1991 | Amplatz et al. | 128/772 |
| 5,045,072 | 9/1991 | Castillo et al. | 604/280 |
| 5,061,254 | 10/1991 | Karakelle et al. | 604/265 |
| 5,069,226 | 12/1991 | Yamauchi et al | 128/772 |
| 5,078,702 | 1/1992 | Pomeranz | 604/280 |
| 5,095,915 | 3/1992 | Engelson | 128/772 |
| 5,129,890 | 7/1992 | Bates et al. | 604/281 |
| 5,333,620 | 8/1994 | Moutafis et al. | 128/772 |
| 5,342,383 | 8/1994 | Thomas | 606/190 |
| 5,452,726 | 9/1995 | Burmeister et al. | 128/772 |
| 5,533,985 | 7/1996 | Wang | 604/264 |

FOREIGN PATENT DOCUMENTS

| | | |
|---|---|---|
| 2 401 668 | 8/1977 | European Pat. Off. . |
| 0 340 304 A1 | 11/1989 | European Pat. Off. . |
| 0 380 102 A1 | 8/1990 | European Pat. Off. . |
| 0 395 098 A1 | 10/1990 | European Pat. Off. . |
| 0 405 823 A2 | 1/1991 | European Pat. Off. . |
| 0 407 965 A1 | 1/1991 | European Pat. Off. . |
| 60-12069 | 1/1985 | Japan . |
| 2-180277 | 7/1990 | Japan . |
| 8-257136 | 10/1996 | Japan . |
| WO 85/01444 | 4/1985 | WIPO . |
| WO 89/09626 | 10/1989 | WIPO . |
| WO 91/00051 | 1/1991 | WIPO . |

OTHER PUBLICATIONS

Tegtmeyer, "Current Problems in Diagnostic Radiology", vol. XVI, No. 2, Mar./Apr., 1987, pp.79–80.

Primary Examiner—Max Hindenburg
Assistant Examiner—Pamela L. Wingood
Attorney, Agent, or Firm—Crompton, Seager & Tufte, LLC

[57] ABSTRACT

An intravascular guidewire providing enhanced steerability and radioscopic visibility. The guidewire has an elongated selectively formable core and a plastic jacket including proximal and distal jacket portions, where the distal jacket portion is further divided into a proximal jacket section and a distal jacket section. The distal jacket portion incorporates means for enhancing the radiopaque properties of the distal jacket portion relative to the proximal jacket portion. The distal jacket section has a different radiopacity than the proximal jacket section, making the distal jacket section more easily viewable under radioscopy. One embodiment provides enhanced steerability with a distal jacket section made of softer material than the proximal jacket section. Another embodiment provides enhanced steerability with a distal jacket cross-section smaller than the proximal jacket cross-section.

8 Claims, 2 Drawing Sheets

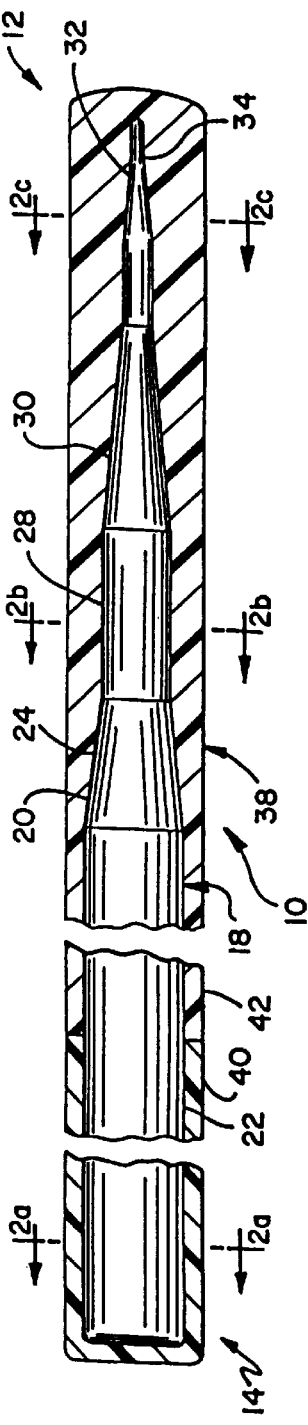
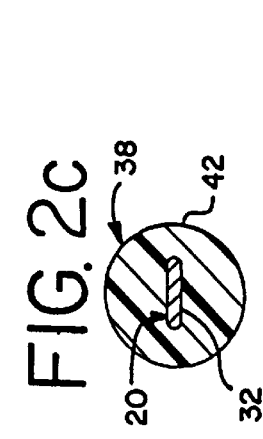
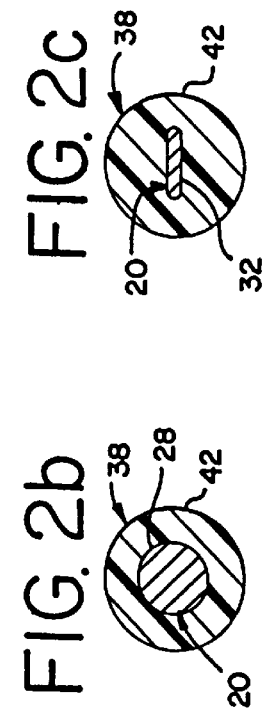
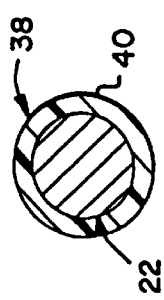
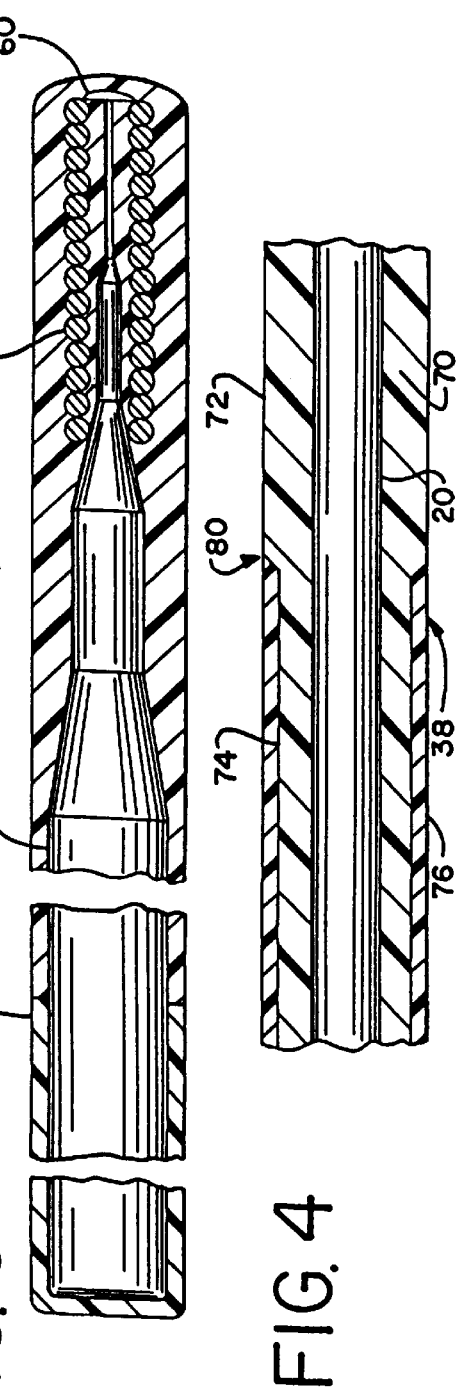

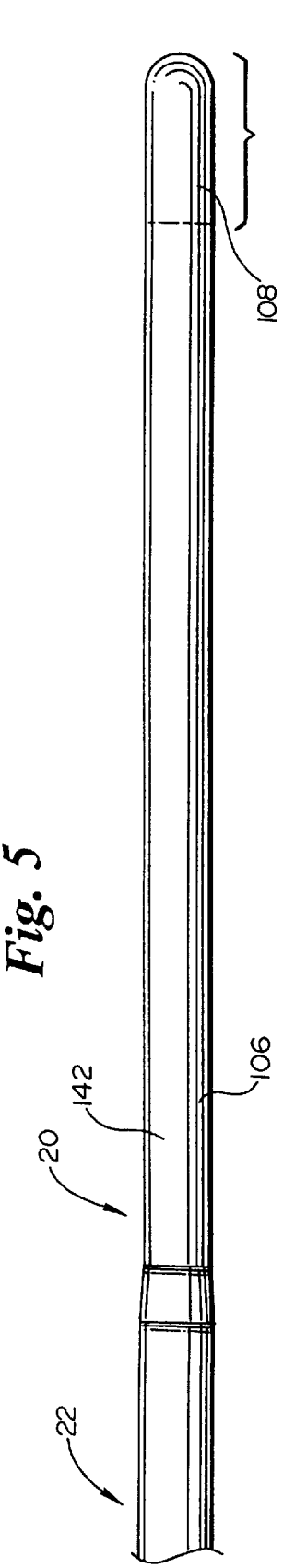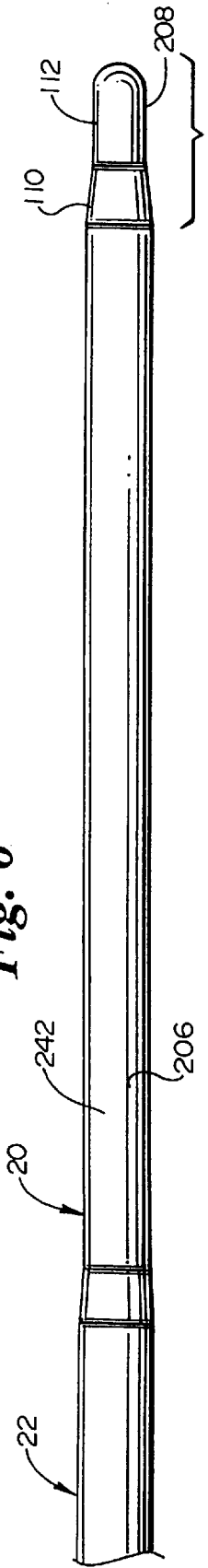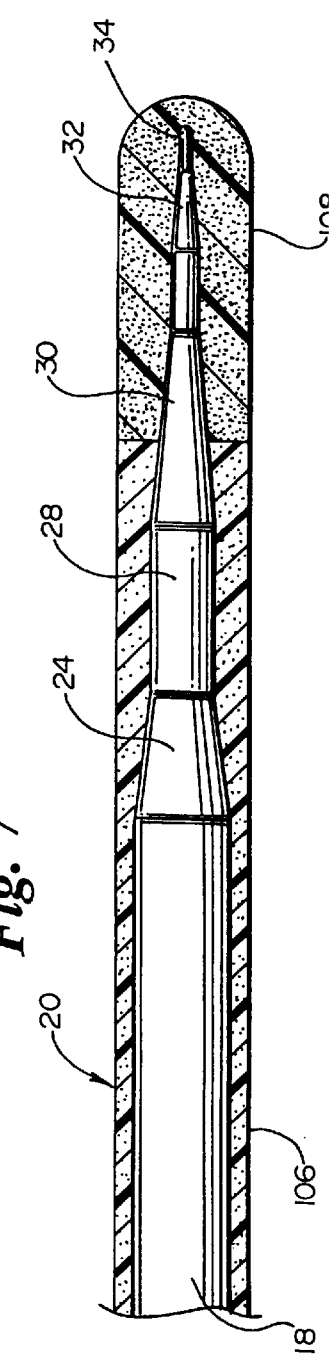

INTRAVASCULAR GUIDEWIRE

BACKGROUND OF THE INVENTION

The present invention relates to intravascular guidewires, and methods of manufacture thereof. In particular, the present invention relates to an intravascular guidewire, and methods for the manufacture thereof, with improved flexibility and radiopacity properties to enhance the use thereof.

Guidewires are used in various procedures in both the coronary regions and the peripheral regions of the body. Various sizes and lengths of guidewires are made to be suitable for various uses and locations in the body. For example, guidewires of a very small diameters, on the order of 0.010 to 0.018 inches may be suitable for use in narrow coronary vessels. Such guidewire may have an extremely floppy distal tip which may be bent or preformed by the physician to facilitate placement of the guidewire at the desired location. Other guidewires have a larger diameter, for example 0.035 inches. These larger diameter guidewires may be especially useful in peripheral regions of the body. Larger diameter guidewires may be provided with very flexible tips or with relatively rigid tips depending upon the particular needs of the patient and the preferences of the physician. Guidewires come in a range of sizes in addition to those discussed above.

Some of the characteristics preferred in guidewires by some physicians include support, the ability to provide a track for a balloon or other device to advance over, and good torsional transmittance. A discussion of these and other preferred characteristics of guidewires is in *Endovascular Surgery*, by Moore, W. S. and Ahn, S. S.; p. 157, W. B. Saunders Co. (1989). One of the characteristics considered desirable by some physicians in a guidewire is that it should be easy to grip and use manually at the proximal portion.

Other characteristics preferred in guidewires by some physicians include extreme flexibility and formability at the distal tip, and an enhanced radiographic signature to facilitate tracking the distal tip. In particular, it is desirable to have a formable distal tip, such that the treating physician may bend the tip to a desired shape for insertion into a particular vessel. It is often desirable that the proximal portion of the guidewire be elastic rather than formable, so that when being advanced through the arterial system, this proximal portion does not permanently deform to the curves encountered. It is also desirable to have the tip be easily visible under fluoroscopy. Further, it is desirable to have a portion of the guidewire just proximal of the tip having a less intense radiopacity than the tip so as not to visibly obscure the vessel after the tip has crossed the lesion. Finally, it is desirable to have the distal tip be extremely flexible, such that the treating physician may maneuver this extremely flexible tip into difficult to reach positions. A more flexible tip is more atraumatic to a vessel and less likely to cause damage.

SUMMARY OF THE INVENTION

According to a first aspect of the invention, there is provided a guidewire, and a method for the manufacture thereof, having a core and a plastic jacket enclosing the core. The plastic jacket comprises a proximal portion formed of a first plastic material and a distal jacket portion formed of a second plastic material. The distal end of the proximal jacket portion and the proximal end of the distal jacket portion are substantially equal outer diameters so as to form a smooth transition between the proximal and the distal jacket portions.

According to another aspect of the invention, there is provided a guidewire, and a method for the manufacture thereof, with a core that is selectively formable in at least a distal portion thereof, and a plastic jacket encasing the selectively formable core. The plastic jacket has a distal portion with a hydrophilic coating and a proximal portion without a hydrophilic coating.

According to another aspect of the invention, there is provided a guidewire, and a method for the manufacture thereof, having a core and a method for the manufacture thereof, having a core that is selectively formable, at least in a distal portion thereof, and a plastic jacket encasing the core. The plastic jacket has a distal portion that is more radiopaque than a proximal portion.

In another embodiment, the distal jacket portion can be further divided into a distal jacket section and a proximal jacket section. The distal jacket section is formed of a softer material than the proximal jacket section, thereby making the distal jacket section more flexible than the proximal jacket section. The distal jacket section can have a reduced cross section than the proximal jacket section, thereby also making the distal jacket section more flexible than the proximal jacket section.

The radiopacity properties of the distal and proximal jacket sections can be varied by loading these sections with differing amounts of radiopaque material. The distal jacket section, for example, can include more radiopaque loading than the proximal jacket section such that the distal jacket section will be more visible under radioscopy than the proximal jacket section.

BRIEF DESCRIPTION OF THE DRAWINGS

FIG. 1 is a sectional view of a first embodiment of the present invention;

FIG. 2a shows a cross section of the embodiment of FIG. 1 along line 2a-2a';

FIG. 2b shows a cross section of the embodiment of FIG. 1 along line 2b-2b';

FIG. 2c shows a cross section of the embodiment of FIG. 1 along line 2c-2c';

FIG. 3 is a sectional view of another embodiment of the present invention;

FIG. 4 is a sectional view of yet another embodiment of the present invention;

FIG. 5 is a side view of yet another embodiment of the present invention;

FIG. 6 is a side view of yet another embodiment of the present invention; and

FIG. 7 is a sectional view of the embodiment of FIG. 5.

DETAILED DESCRIPTION OF THE PREFERRED EMBODIMENTS

Referring to FIG. 1, there is depicted a first preferred embodiment of the present invention. This embodiment is an intravascular guidewire 10. This guidewire 10 has a distal end 12 and a proximal end 14. The guidewire 10 may be approximately 180 to 300 centimeters in length and have an outside diameter of approximately 0.010 to 0.035 inches. Other lengths and diameters may be provided so that a range of sizes of guidewires may be available suitable for the different needs of various individual patients and the preferences of physicians. Such other sizes are contemplated within the scope of the present invention and of this embodiment in particular.

The guidewire 10 includes a core 18. The core may be made of a strong, yet flexible material, such as a metal, like stainless steel or nitinol, or other materials, or combinations thereof. In a preferred embodiment, the core 18 is made at least in part of a selectively formable metallic material, as explained in more detail below. The core 18 extends from the distal end 12 to the proximal end 14 of the guidewire 10.

In a preferred embodiment, the core 18 includes a distal portion 20 and a proximal portion 22. The proximal and distal portions are preferably formed of a single metallic wire. The distal portion 20 has a smaller cross section than the proximal portion 22 to impart greater flexibility to the distal end of the guidewire. In a preferred embodiment, the distal portion 20 of the guidewire comprises a series of stages or regions of tapered portions and portions of uniform cross section, as explained in more detail below. The series of stages of tapered portions and portions of uniform cross section are intended to impart increasing levels of flexibility to the guidewire toward the distal end.

In this embodiment, the proximal portion 22 of the core 18 has a diameter of approximately 0.010 to 0.018 inches. FIG. 2a shows a cross section of the guidewire in the proximal portion 22. The proximal portion 22 of the core 18 extends from a proximal end of the guidewire 10 to a proximal end of the distal portion 20 of the core 18. In this embodiment, the distal portion 20 of the core 18 is approximately 10.50 inches in length.

The distal portion 20 of the core includes a first region 24 immediately adjacent to, and distal of, the proximal portion 22. This first region 24 of the distal portion 20 of the core is approximately 2.0 inches in length. In the first region 24, the core 18 tapers from the diameter of the proximal portion 20 (e.g., 0.018 inches) to a diameter of approximately 0.009 inches. In this first region 24, the core has a circular cross section.

The distal portion 20 of the core next includes a second region 28 immediately adjacent to, and distal of, the first region 24. This second region 28 of the distal portion 20 of the core is approximately 4.0 inches in length. FIG. 2b shows a cross section of the guidewire in this region. The second region 28 is a region of approximately uniform cross section. In this second region 28, the core also preferably has a circular cross section.

The distal portion 20 of the core next includes a third region 30 immediately adjacent to, and distal of, the second region 28. This third region 30 of the distal portion 20 of the core is approximately 2.0 inches in length. In the third region 30, the core 18 tapers from the diameter of the second region 28 (e.g., 0.0090 inches) to a diameter of approximately 0.00525 inches. In this third region 30, the core also has a circular cross section.

The distal portion 20 of the core next includes a fourth region 32 immediately adjacent to, and distal of, the third region 30. This fourth region 32 of the distal portion 20 of the core is approximately 1.75 inches in length. In the fourth region 32, the core 18 is flattened toward a distal end 34 thereof to form a ribbon shape having dimensions of approximately 0.010 by 0.00225 inches. FIG. 2c shows a cross section of the guidewire in this region. The ribbon shape of this region causes the guidewire to tend to flex in one plane thereby facilitating the use thereof. In the fourth region 32, the length of the distal flattened portion is approximately 0.5 inches, the length of the portion of circular cross section is approximately 0.7 inches, and a transition zone between these portions has a length of approximately 0.7 inches.

The distal portion 20 of the core wire, including the various regions of the tapered and uniform cross section, may be formed by methods known in the art, such as chemical washes, polishes, grinding, or compressing.

The guidewire 10 also includes a plastic jacket 38 extending from the proximal end 14 to the distal end 12. In a first preferred embodiment, the plastic jacket 38 is formed of a proximal jacket portion 40 and a distal jacket portion 42. The outside diameter of the plastic jacket 38 in this embodiment is approximately 0.035 inches although other diameters may be provided for guidewires of other dimensions.

The distal jacket portion 42 is approximately 18 inches in length and extends proximally from the distal end of the guidewire 10. The distal end of the distal jacket portion 42 extends over and covers the distal end of the core wire 18. The proximal jacket portion 40 extends from the proximal end of the guide wire 10 distally. In this embodiment, the proximal end of the distal jacket portion 42 substantially abuts the distal end of the proximal jacket portion 40. At the location at which the proximal and distal jacket portions abut, the outside diameters of the jacket portions are substantially the same and form a smooth transition at that location so that the guidewire can be readily inserted into, and removed within, a catheter or vessel or that a catheter or other device can be readily advanced over the guidewire.

These two jacket portions are provided to yield features related to functions specifically associated with their respective locations. In this embodiment, the proximal jacket portion 40 is made of polytetrafluoroethylene material and the distal jacket portion 42 is made of polyurethane. Alternatively, the proximal jacket portion 40 may be made of another material or combination of materials, such as fluororesins, such as Kynar ($CH_2CF_2$), high density polyethylene, Delrin (polyacetal), Hytrel or polypropylene. The distal jacket portion 42 may be made of other polymers or co-polymers, or elastomers, or fluoroelastomers or silicone, Hytel or nylon.

In a preferred embodiment, the distal jacket portion has a hydrophilic coating applied to it to make the surface highly lubricous when it comes in contact with a fluid such as blood. The hydrophilic coating is believed to improve the biocompatibility of the guidewire. This is based in part on observations that hydrophilic surfaces are generally less thrombogenic, and more specifically, tend to exhibit reduced platelet activation and aggravation compared to hydrophilic surfaces. In a preferred embodiment, the composition of the coating is a mixture of a hydrogel and a polyurethane in an organic/water solvent mixture. The solution mixture is applied to the distal jacket portion 42 and dried. In a preferred embodiment, polyvinyl pyrrolidone (PVP) is used as a hydrogel and commercial polyurethanes such as Dow (Pellethane 2363 Series) or Thermedics (the Tecophane of Tecoflex families) may be used. A polymer blend having an affinity to the polyurethane substrate of the distal jacket portion (via the urethane and the solution) is used while the other component is a slippery otherwise water-soluble material. The hydrogel will not tend to dissolve away because it is ensnared with the water insoluble polyurethane.

As an alternative to using hydrophilic coating, a different coating may be applied to the guidewire jacket to enhance its lubriciousness. Such a coating may be a silicone coating or other lubricous material.

In a preferred embodiment, the hydrophilic coating is applied only to a distal portion of the guidewire, and, in particular, only to the distal jacket portion 42. This is facilitated because the preferred hydrophilic coating is formulated to adhere to the urethane material of the distal jacket portion but not adhere to many different materials including the preferred material of the proximal jacket.

As mentioned above, the proximal jacket portion is made of polytetrafluoroethylene which also provides a low friction surface though not as low friction as that of the distal jacket portion with the hydrophilic coating applied. It is advantageous for the proximal portion of the guidewire to have a low friction surface in order to traverse a catheter lumen or a vessel. However, because the proximal portion of the guidewire will likely be in a portion of the vasculature not as tortuous as the distal portion, it would not require a surface of as high lubricity as the distal portion and, therefore, polytetrafluoroethylene is a good choice of materials.

Moreover, this combination of low friction surfaces has the additional advantage that a very low friction surface, such as one having a hydrophilic coating, is used only on the distal portion of the guidewire. A very low friction surface, such as one having a hydrophilic coating, would be so slippery that it would be difficult for a physician to handle if it were on the proximal end as well. Accordingly, at the proximal end of the guidewire, this embodiment includes a surface that is easy for the physician who would be manipulating the guidewire from the proximal end to handle and yet is of sufficiently low friction so that it can readily traverse portions of the patient's vessels and provide good guidewire movement in a catheter.

It is also preferred that the distal portion of the guidewire be provided with enhanced radiopaque properties. In the preferred embodiment, this is done by loading the material from which the distal jacket 42 is made with radiopaque materials such as barium, bismuth or tungsten. The loading of the distal jacket of polyurethane with a radiopaque material enhances the ability of a physician to observe the position of the distal end of the guidewire in the body of the patient by means of fluoroscopy.

In a preferred embodiment, the proximal jacket portion 40 of polytetrafluoroethylene is heat shrunk onto the core wire. The distal jacket portion 42 is installed over the core wire by heating a sleeve of polyurethane to a temperature until it is reformed around the core wire. The proximal and distal jackets may be finished by a centerless grinding method so that the transition between the jacket portions is smooth.

In a further embodiment, the guidewire has a core that is selectively formable at least in a distal portion thereof. By a selectively formable core, it is meant that the wire from which the core is made may be bent to a particular shape and that the shape will be maintained by the wire. This allows the physician to impart a particular shape to the guidewire, by bending or kinking it, for example, to facilitate its placement into a patient's vasculature. To provide this selective formability, in a preferred embodiment, the entire core wire may be made of stainless steel. Other materials may be used to provide this feature. The use of a formable material, such as stainless steel, provides advantages in the guidewire over materials that cannot be formed, such as superelastic materials like nitinol. Superelastic materials, like nitinol, are so resilient that they tend to spring back to their original shape even if bent, thus are not formable. Although superelastic material may be provided with a "preformed" memory shape, such a preformed shape is typically determined in the manufacture of the guidewire and cannot readily be altered or modified by the physician by simply bending the guidewire prior to use. Although use of superelastic materials such as nitinol in guidewire applications may provide some advantages in certain uses, a formable core, such as of stainless steel, which can be formed by the physician to a shape suitable for a particular patient or preferred by that physician, provides an advantage that cannot be obtained with a superelastic core guidewire.

In a further preferred embodiment, the guidewire may include a core wire of a material having formable properties at a distal portion thereof and non-formable (e.g., superelastic properties) proximally. Such a construction would provide advantages in certain guidewire usages. A guidewire having these properties could be formed by using a superelastic material such as nitinol for the core wire and reducing its superelasticity in a distal portion thereof. This may be effected by heating the distal end of the superelastic core wire. Another means to reduce the superelastic properties of a distal end of the core wire would be to shape it mechanically, e.g., flattening it. Other methods of reducing the superelastic properties of the core wire may also be used. With a core wire having this dual combination of a formable distal portion and a superelastic proximal portion, desired shapes could be imparted by a physician to the distal end of the guidewire to facilitate making turns, etc., in tortuous vessel passages, while in the same guidewire the more proximal portion would possess superelastic properties to allow it to follow the distal portion through the tortuous passages without permanently deforming. This combination of formable and non-formable properties in the core wire may also be provided by using more than one material for the core wire or more than one wire.

FIG. 3 shows another embodiment of the present invention. This embodiment of the guidewire is similar in some respects to the embodiments of the guidewire, described above. Although this embodiment of the guidewire may be provided in large sizes (e.g., 0.035 inches), this embodiment is especially suitable for a guidewire of a smaller diameter, e.g., having an outer diameter of approximately 0.018 inches. If provided in a guidewire of smaller diameter, the diameter of the core wire and plastic jacket would be correspondingly smaller. Like the embodiment described above, this guidewire includes a core 52 surrounded by a plastic jacket 54. The core 52 is preferably of a selectively formable material, as described above. In addition, in this embodiment, a marker 56 is provided at a distal end 58 of the guidewire 50. This marker 56 is located around the distal portion of the core wire 52 underneath the plastic jacket 54. In this embodiment, the marker 56 is a coil spring. Alternatively, the marker may be a ribbon, another wire, a gold plating on core 52, or any other similar component. A tip 60 may be provided at the distal end of the core wire 52 to facilitate placement and connection of the marker 56.

The marker 56 may be made of platinum or stainless steel or other material. The marker 56 may be provided with radiopaque properties by selecting a material such as platinum. This may be in addition or as an alternative to providing radiopaque properties in the jacket portion through the use of loading with radiopaque material. The use of a radiopaque marker may be preferred in smaller diameter guidewires where the plastic jacket, even if loaded with a radiopaque material, is of such a small size that it could be difficult to discern under fluoroscopy.

FIG. 4 shows another embodiment of the present invention. In the embodiment in FIG. 4, a core wire 20 extends from a distal to a proximal end of the guidewire. As in the embodiment described above, the core wire 20 is surrounded by a core wire jacket 38. In this embodiment, the core wire jacket 38 is comprised of a first jacket 70. The first jacket 70 of this embodiment is comprised of a first portion 72 and a second portion 74. The core wire jacket 38 also includes a second jacket 76. The second jacket 76 covers the first jacket 70 over the second portion 74 thereof. The second jacket 76 may correspond to the proximal jacket of the previous embodiments. The second jacket 76 may be a thin tubing that is heat shrunk onto the first jacket 70 over a proximal portion thereof. Alternatively, the second jacket 76 may be applied by other methods, such as by spraying, dipping, etc.

In a preferred embodiment, the outer diameter of the second jacket 76 when it is in position surrounding the first jacket 70 is approximately the same as the outer diameter of the first jacket 70 in the first portion 72 thereof at least in an area 80 of the guidewire where the second jacket 76 ends so that the overall diameter of the guidewire through this area 80 is substantially uniform. This uniformity may be further enhanced by polishing, grinding, or other means. To further provide for this uniformity in diameter, the second portion 74 of the first jacket 70 may be provided with a diameter that is less than that of the first portion 72 of the first jacket 70. This reduction in diameter may be formed by grinding, stretching, chemical erosion, or other means.

In a preferred embodiment, the second jacket 76 covers the proximal portion of the guidewire and an exposed first portion 72 of the first jacket 70 extends to a distal end of the guidewire. The first jacket 70 and second jacket 76 may be provided with properties specifically directed to their respective functions, as explained above in regard to the embodiment of the guidewire in which the jackets are in an abutting relationship. For example, the first jacket 70 may be made of polyurethane and the second jacket 76 may be made of a polytetrafluoroethylene material. A hydrophilic coating may be applied to the first jacket 70 in the first portion 72 thereof to enhance lubricity, as explained above. If this embodiment of the guidewire is intended for use in peripheral regions of the body, it may have an outside diameter of approximately 0.035 inches. Other dimensions may be suitable as well for other size guidewires. As in the previously described embodiments, the core 20 may be a material such as stainless steel or nitinol and may have formable properties in at least a portion thereof.

FIG. 5 shows another preferred embodiment of the present invention. Distal jacket portion 142 is divided into a proximal jacket section 106 and distal jacket section 108. In one embodiment of this invention, distal jacket section 108 is about one inch in length. The length of distal jacket section 108 can be greater or less than this length depending upon the desired steerability characteristics of the guidewire.

Preferably, distal jacket section 108 has a hardness less than the hardness of proximal jacket section 106. In one embodiment of this invention, distal jacket section 108 has a hardness of between about 80 A and 85 A Durometer, which is softer than proximal jacket section 106 which has a hardness about of 93 A Durometer. This decreased hardness in distal jacket section 108 relative to proximal jacket section 106 allows for greater flexibility in distal jacket section 108.

The distal jacket section 108 is preferably more radiopaque than proximal jacket section 106. In another embodiment of this invention, distal jacket section 108 is about 80 percent (80%) to 90 percent (90%) loaded with tungsten, giving it greater radiopacity than proximal jacket section 106 which is about 40 percent (40%) to 65 percent (65%) loaded with tungsten. Those skilled in the art would know that radiopaque material such as barium, bismuth or a combination thereof are suitable for loading. Those skilled in the art would also know that changing the loading material can impact the required percent loading to obtain the degree of radiopacity obtained from a different loading material. The difference in radiopacity gives distal jacket section 108 a relatively greater visibility under radioscopy, while allowing proximal jacket section 106 to be visible under radioscopy as well. In this way, the location of both distal portion 20 in general and distal jacket section 108 in particular, may be determined.

FIG. 6 shows another preferred embodiment of the present invention. Distal jacket portion 242 is divided into proximal jacket section 206 and distal jacket section 208. Distal jacket section 208 includes a distal jacket section taper 110 proximally, and a distal reduced section 112 distally. The cross section narrows proceeding from proximal jacket section 206 through distal jacket section taper 110 to distal reduced section 112. The reduced cross section of distal reduced section 112 gives greater flexibility to distal jacket section 208 relative to proximal jacket section 206, providing enhanced steerability through tortious vessel paths. In one embodiment of this invention, the length of distal jacket section taper 110 and distal reduced section 112 combined is about one inch. The length of distal jacket section taper 110 and distal reduced section 112 can be greater or less than this length depending upon the desired steerability characteristics of the guidewire. Distal section taper 110 and reduced section 112 may be formed by methods known in the art, such as chemical washes, polishes, grinding, or compressing.

FIG. 7 shows a longitudinal cross section of the guidewire of FIG. 5 illustrating the differences in radiopaque material loading relative to distal portion 20 of the core. Distal jacket section 108 is more heavily loaded with radiopaque materials than proximal jacket section 106. In this embodiment of the invention, core 18 is enclosed in plastic having lower radiopaque material loading in proximal jacket section 106 than in distal jacket section 108.

It is intended that the foregoing detailed description be regarded as illustrated rather than limiting and that it is understood that the following claims including all equivalents are intended to define the scope of the invention.

What is claimed is:

1. A guidewire comprising:
    an elongated core having a length, a width, proximal end, distal end, and an axial surface extending the length of said elongated core; and
    a plastic jacket extending around said axial surface of said elongated core, said plastic jacket including a proximal jacket portion and a distal jacket portion, said portions formed of a plastic material, wherein said distal jacket portion incorporates means for enhancing the radiopaque properties of said distal jacket portion relative to said proximal jacket portion;
    said distal jacket portion having a distal jacket section and a proximal jacket section, said proximal jacket section having a different radiopacity than said distal jacket section wherein said distal jacket section radiopacity is greater than said proximal jacket section radiopacity, and said distal jacket section is at least 80% loaded by weight with radiopaque material; and
    said distal jacket section including a softer material than said proximal jacket section and including a plastic atraumatic distal tip disposed distally of said distal end of said core.

2. The guidewire of claim 1, wherein said distal jacket section has a length of about 1 inch.

3. The guidewire of claim 1, wherein said distal jacket section has a smaller cross section than said proximal jacket section.

4. The guidewire of claim 3, wherein said distal jacket section has a length of about 1 inch.

5. The guidewire of claim 1, wherein said distal jacket section has a Durometer value in the range of about 80 A to about 85 A, and said proximal jacket section has a Durometer value of about 93 A.

6. The guidewire of claim 1, wherein said core comprises stainless steel.

7. The guidewire of claim 1, wherein said radiopaque material is a compound containing tungsten.

8. The guidewire of claim 1, wherein said means for enhancing the radiopaque properties of said distal jacket section relative to said proximal jacket section include the incorporation of a radiopaque material within said plastic of said distal jacket portion.

* * * * *